(12) United States Patent
Von Schuckmann

(10) Patent No.: US 12,083,269 B2
(45) Date of Patent: Sep. 10, 2024

(54) HAND-HELD DEVICE FOR DISPENSING SPRAYABLE SUBSTANCES IN A PORTIONED MANNER

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 867 days.

(21) Appl. No.: 17/260,010

(22) PCT Filed: Jun. 17, 2019

(86) PCT No.: PCT/EP2019/065888
§ 371 (c)(1),
(2) Date: Jan. 13, 2021

(87) PCT Pub. No.: WO2020/015943
PCT Pub. Date: Jan. 23, 2020

(65) Prior Publication Data
US 2021/0316092 A1 Oct. 14, 2021

(30) Foreign Application Priority Data
Jul. 16, 2018 (DE) ...................... 10 2018 117 106.4

(51) Int. Cl.
*A61M 15/00* (2006.01)

(52) U.S. Cl.
CPC .... *A61M 15/0091* (2013.01); *A61M 15/0013* (2014.02); *A61M 15/0025* (2014.02);
(Continued)

(58) Field of Classification Search
CPC .............. A61M 15/00; A61M 15/0091; A61M 15/0013; A61M 15/0025; A61M 15/0073;
(Continued)

(56) References Cited

U.S. PATENT DOCUMENTS

| | | | | |
|---|---|---|---|---|
| 3,789,843 A | * | 2/1974 | Armstrong | A61M 15/0091 128/200.23 |
| 4,664,107 A | * | 5/1987 | Wass | A61M 15/0091 128/200.23 |

(Continued)

FOREIGN PATENT DOCUMENTS

| | | |
|---|---|---|
| EP | 0 414 536 A2 | 2/1991 |
| EP | 0 490 797 A1 | 6/1992 |

(Continued)

OTHER PUBLICATIONS

International Search Report of PCT/EP2019/065888, mailed Oct. 23, 2019.

*Primary Examiner* — Justine R Yu
*Assistant Examiner* — Matthew R Moon
(74) *Attorney, Agent, or Firm* — Collard & Roe, P.C.

(57) ABSTRACT

A hand-held device for metered dispensing of sprayable substances, in particular inhaler medicaments, includes a housing and a cartridge which can be displaced into a dispensing position by a pressure application relative to the housing, wherein the housing has a mouthpiece, wherein the cartridge can be displaced initially into a ready-to-dispense position and a dispensing spray process can be triggered by sucking in, wherein the displacement of the cartridge can be executed by tensioning a spring supported on the housing and acting on the cartridge. The spring is displaced into the position to perform a spraying process, but is hindered by a counterforce that can be deactivated by application of a negative pressure through the mouthpiece of the hand-held device A valve flap is moved by the negative pressure and cancels a mechanical block of the movement of the cartridge.

17 Claims, 13 Drawing Sheets

(52) U.S. Cl.
CPC ...... *A61M 15/0073* (2014.02); *A61M 15/009* (2013.01); *A61M 2205/3331* (2013.01); *A61M 2205/8281* (2013.01)

(58) Field of Classification Search
CPC ........ A61M 15/009; A61M 2205/3331; A61M 2205/8281
See application file for complete search history.

(56) References Cited

U.S. PATENT DOCUMENTS

| | | | |
|---|---|---|---|
| 5,447,150 | A | 9/1995 | Bacon |
| 6,866,038 | B2 * | 3/2005 | Bacon .................... F16K 7/068 128/200.14 |
| 7,814,900 | B2 * | 10/2010 | Bacon ............... A61M 15/0091 128/200.14 |
| 8,474,447 | B2 | 7/2013 | Von Schuckmann et al. |
| 10,729,862 | B2 * | 8/2020 | Pieters .............. A61M 15/0091 |
| 10,967,140 | B2 * | 4/2021 | Petit .................... A61M 15/009 |
| 2008/0178872 | A1 | 7/2008 | Genova et al. |

FOREIGN PATENT DOCUMENTS

| | | |
|---|---|---|
| EP | 2 300 084 B1 | 5/2013 |
| WO | 2004/028608 A1 | 4/2004 |
| WO | 2008/142015 A2 | 11/2008 |
| WO | 2009/037085 A1 | 3/2009 |

* cited by examiner

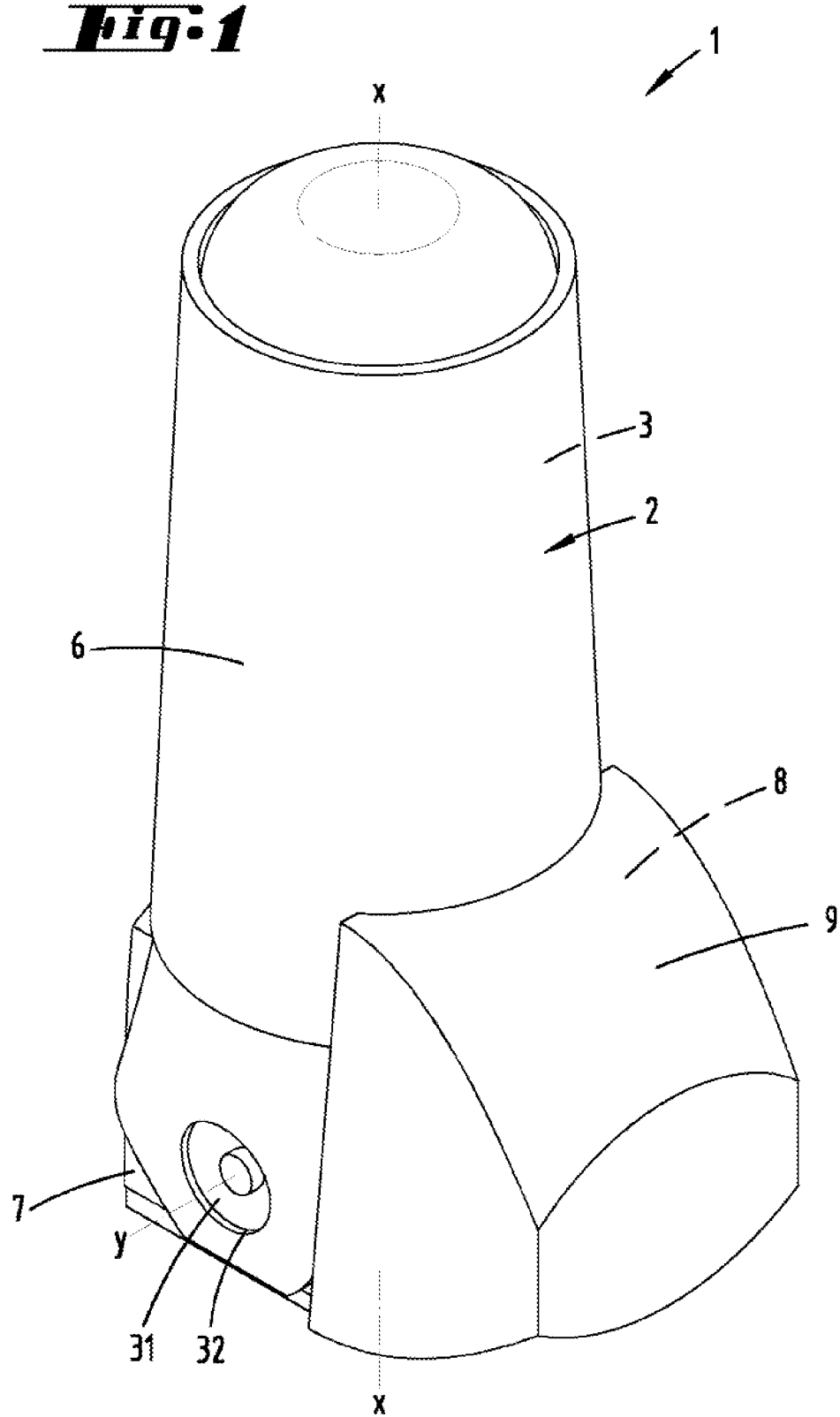

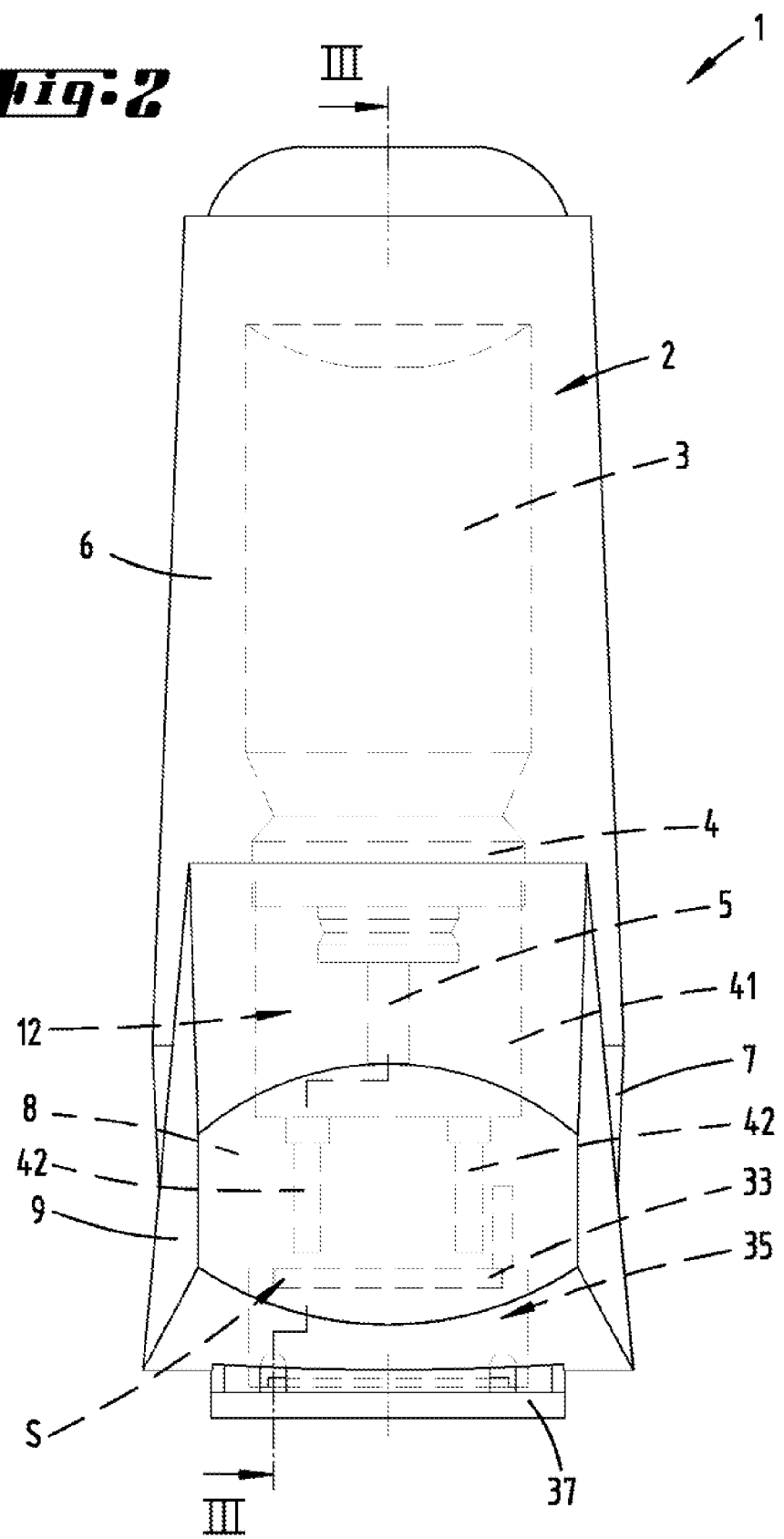

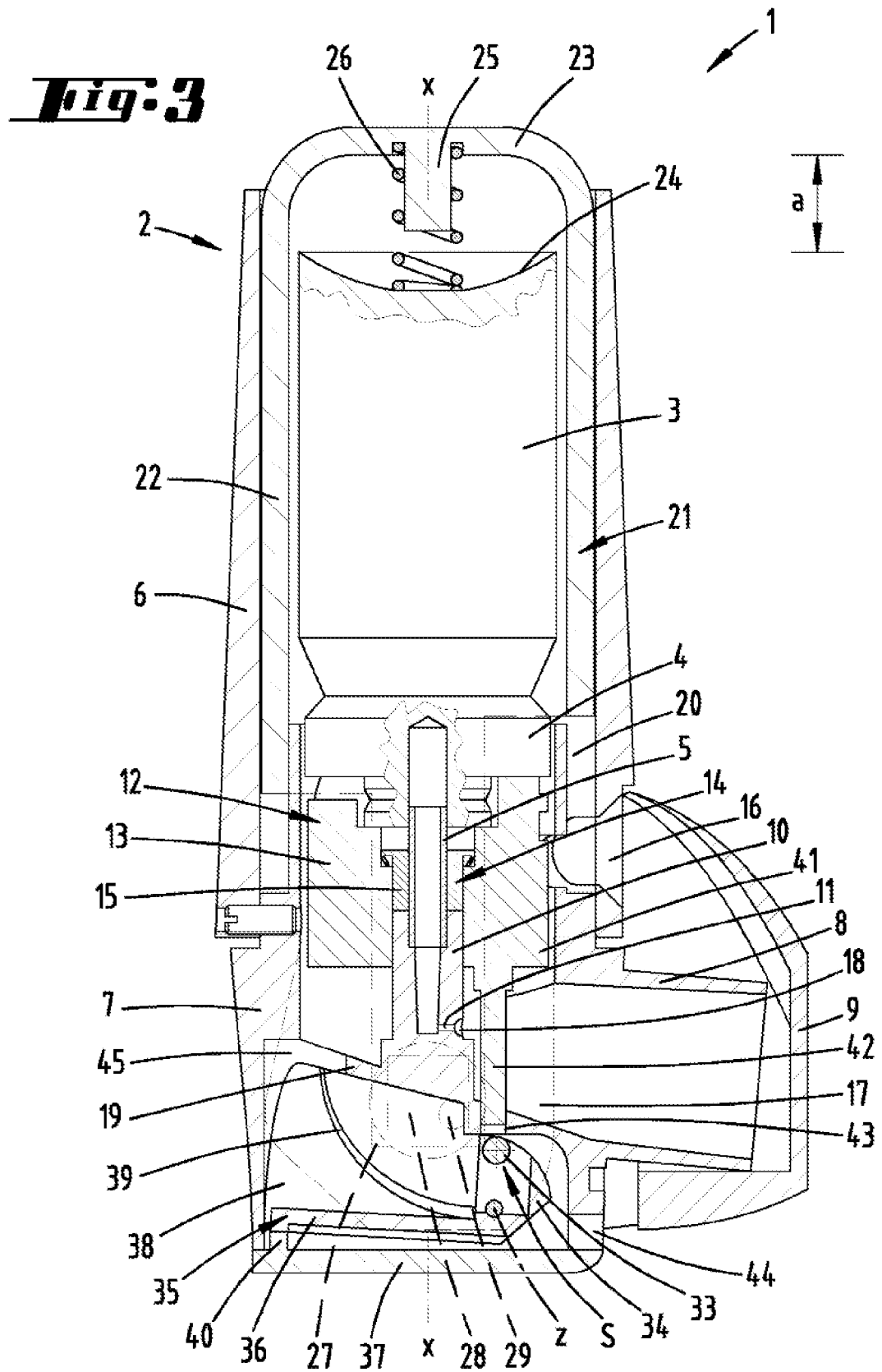

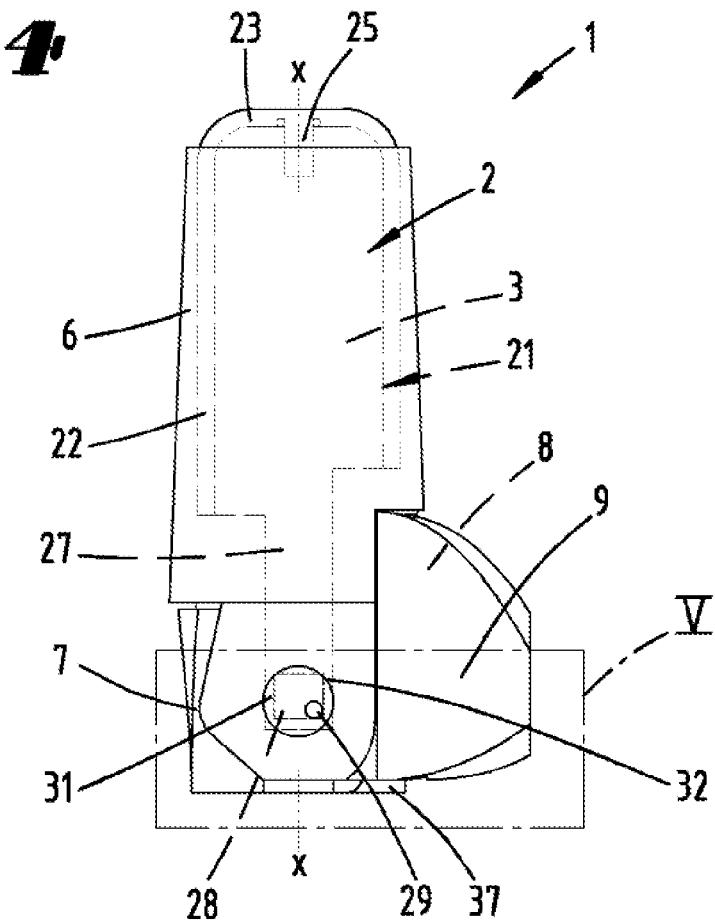
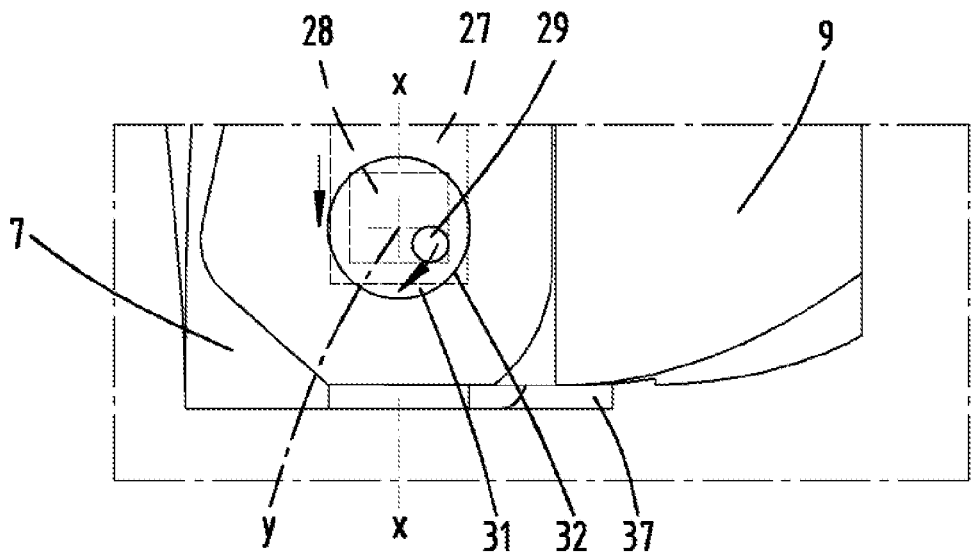

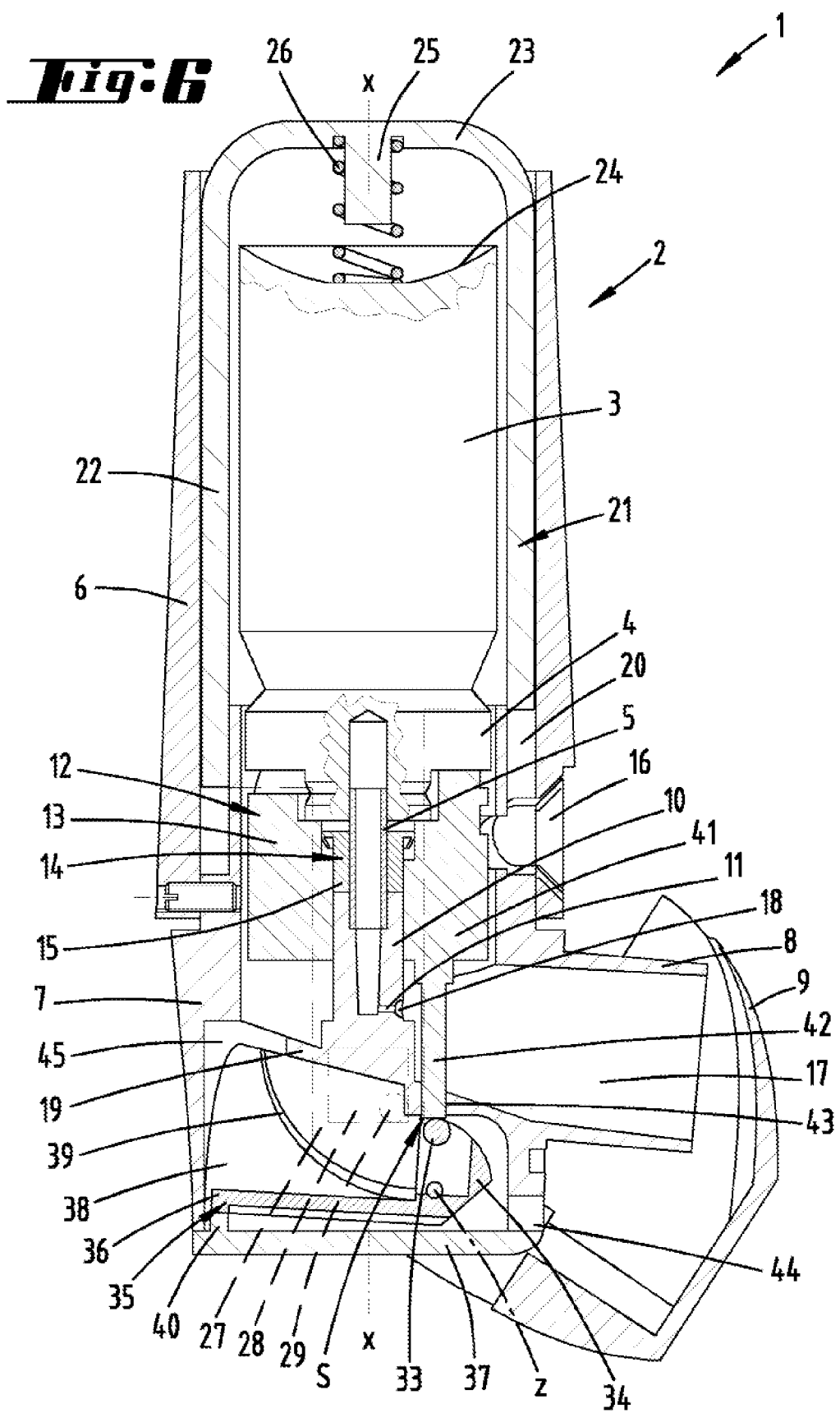

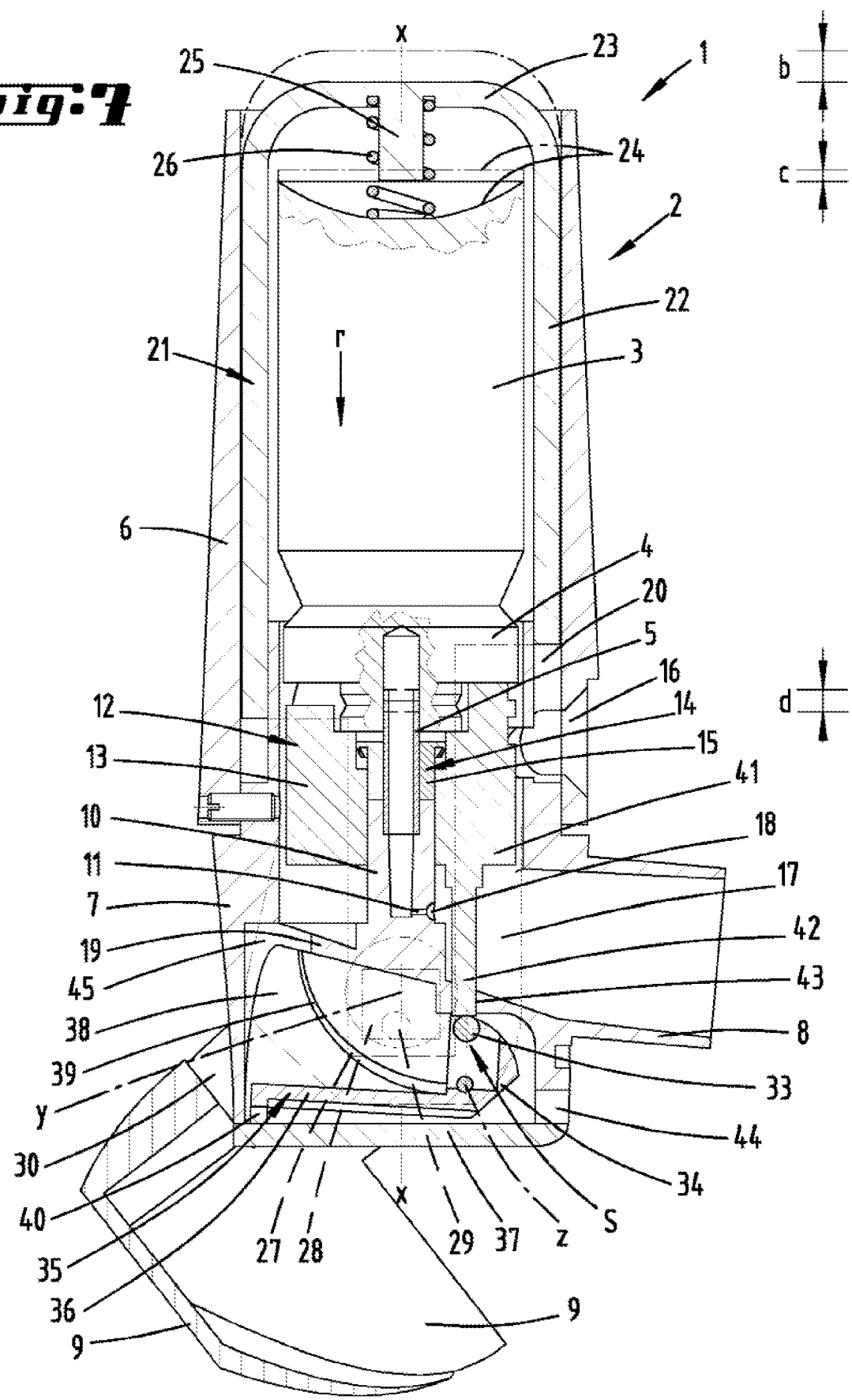

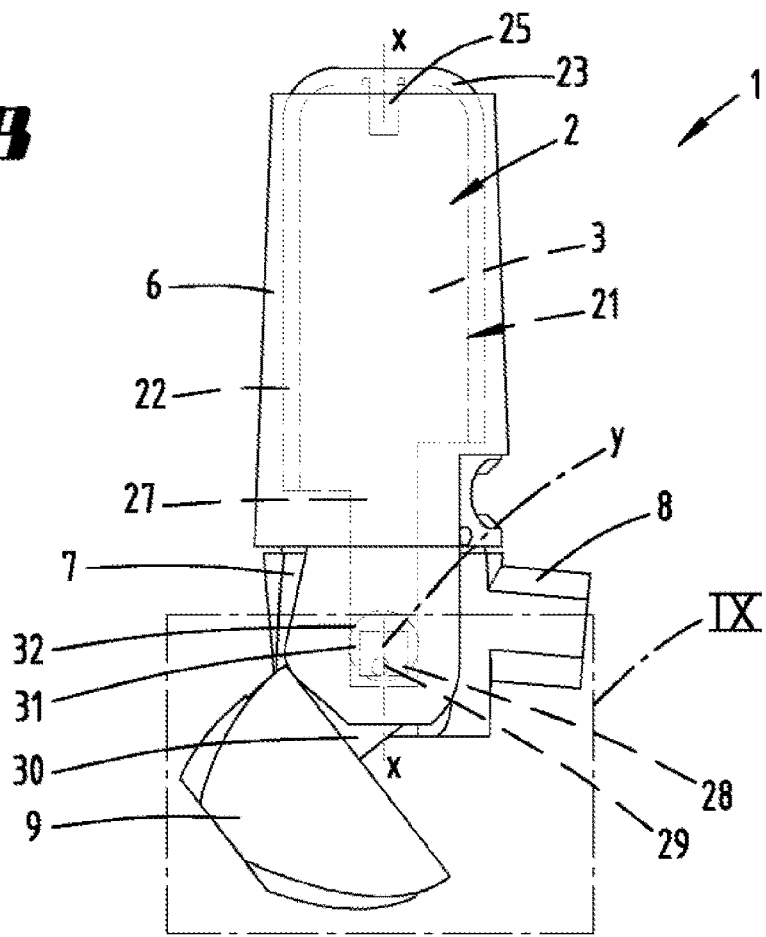
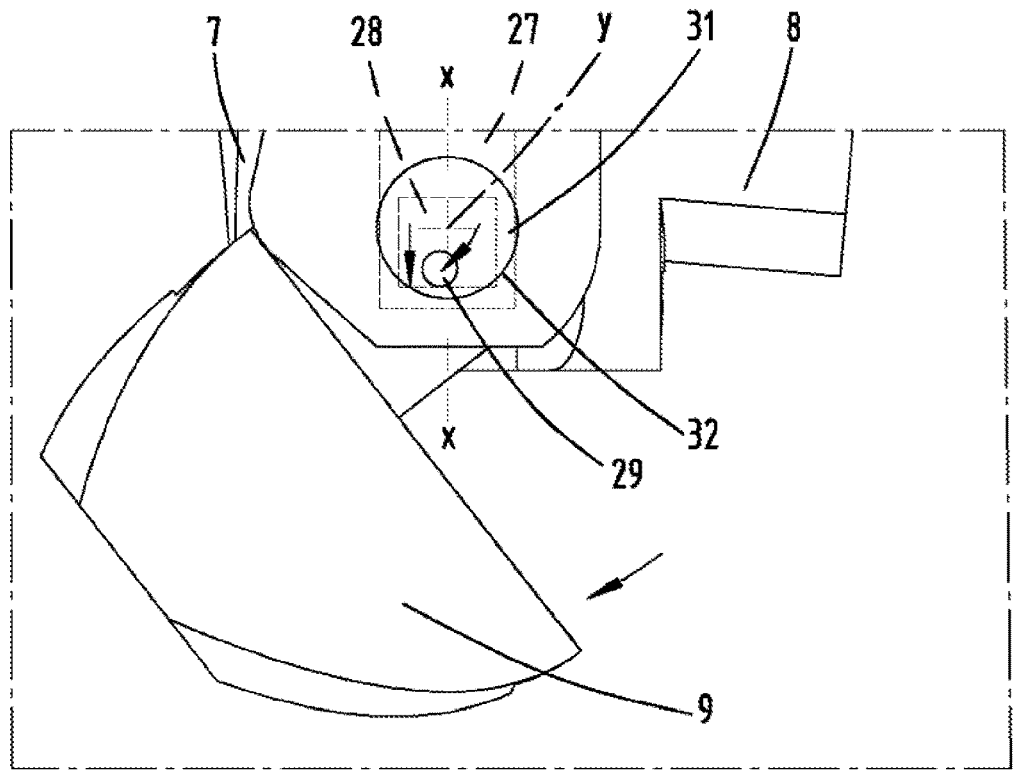

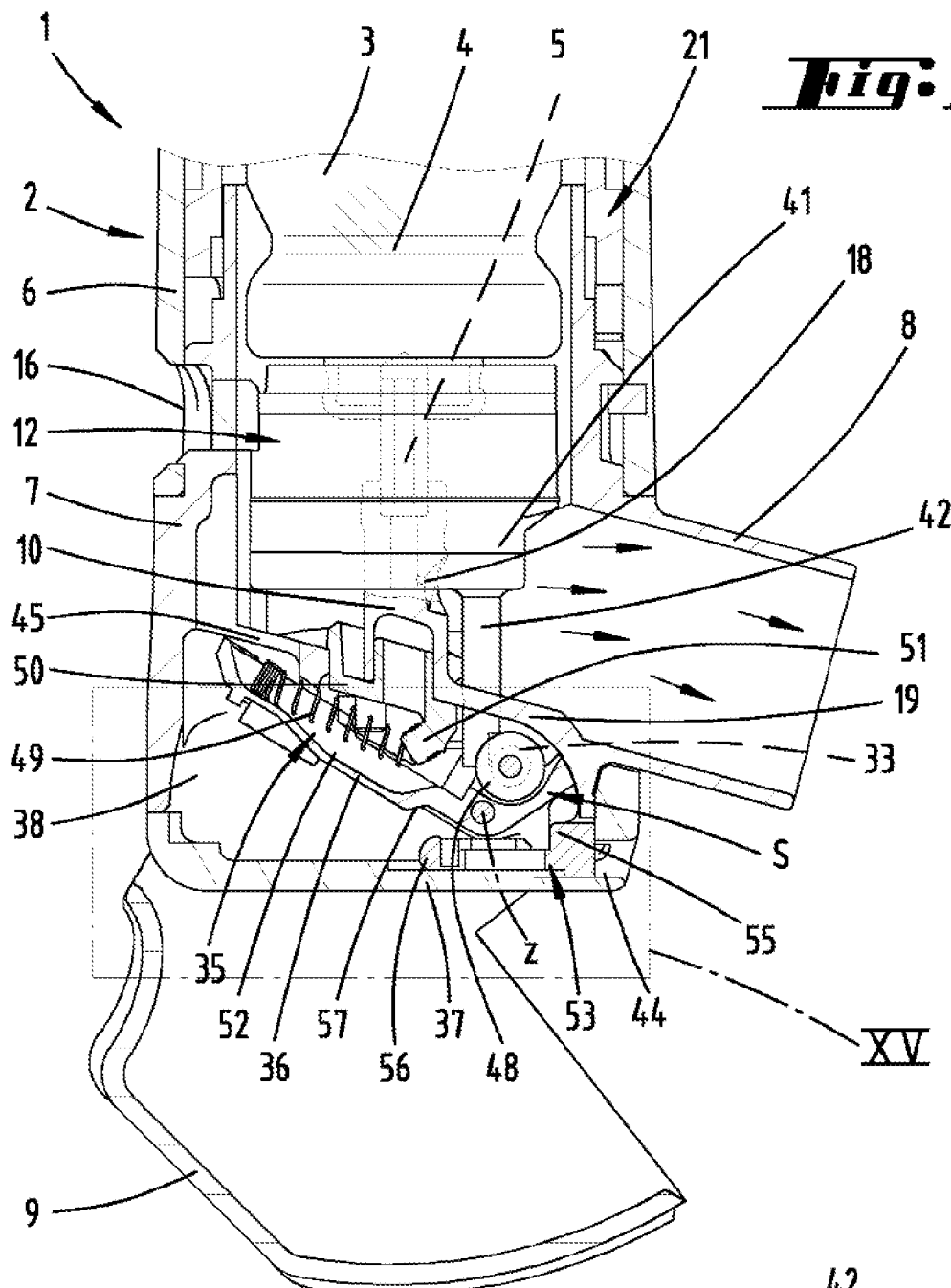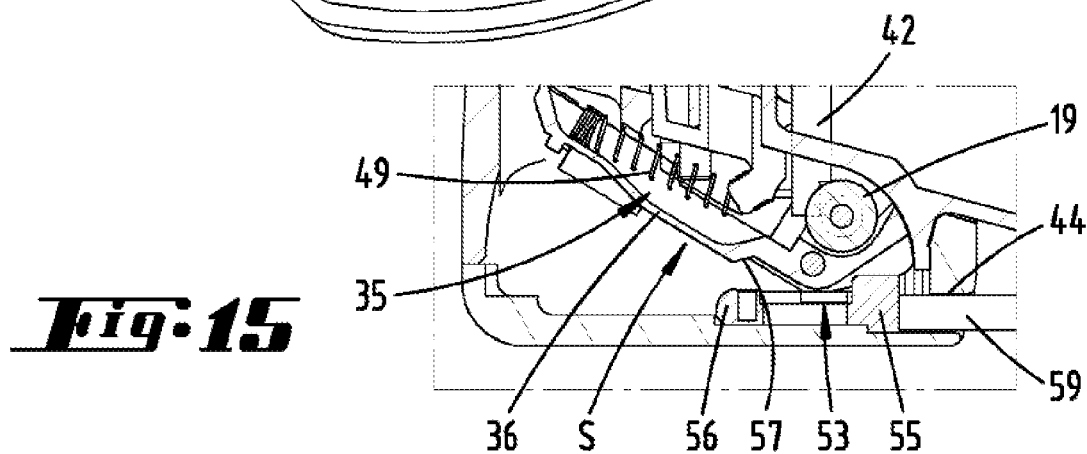

HAND-HELD DEVICE FOR DISPENSING SPRAYABLE SUBSTANCES IN A PORTIONED MANNER

CROSS REFERENCE TO RELATED APPLICATIONS

This application is the National Stage of PCT/EP2019/065888 filed on Jun. 17, 2019 which claims priority under 35 U.S.C. § 119 of German Application No. 10 2018 117 106.4 filed on Jul. 16, 2018, the disclosure of which is incorporated by reference. The international application under PCT article 21(2) was not published in English.

FIELD OF TECHNOLOGY

The invention relates to a hand-held device for metered dispensing of sprayable substances, in particular inhaler medicaments, comprising a housing and a cartridge which can be displaced into a dispensing position by a pressure application relative to the housing, wherein the housing has a mouthpiece, wherein furthermore the cartridge can be displaced initially into a ready-to-dispense position and when the cartridge is located in the ready-to-dispense position, a dispensing spray process can be triggered by sucking in, wherein furthermore the displacement of the cartridge into the ready-to-dispense position can be executed by tensioning a spring supported on the housing and acting on the cartridge, wherein the spring acting on the cartridge is displaced into the position to perform a spraying process, but is hindered from this by a counterforce, which counterforce can be deactivated by the user as a result of the application of a negative pressure through the mouthpiece of the hand-held device, wherein a valve flap is moved by the negative pressure, which cancels a mechanical block of the displacement of the cartridge from the ready-to-dispense position into the dispensing position.

The invention further relates to a hand-held device for metered dispensing of sprayable substances, in particular inhaler medicaments, comprising a housing and a cartridge which can be displaced into a dispensing position by a pressure application relative to the housing, wherein the housing has a mouthpiece, wherein furthermore the cartridge can be displaced initially into a ready-to-dispense position and when the cartridge is located in the ready-to-dispense position, a dispensing spray process can be triggered by sucking in, wherein furthermore the displacement of the cartridge into the ready-to-dispense position can be executed by tensioning a spring supported on the housing and acting on the cartridge, wherein the spring acting on the cartridge is displaced into the position to perform a spraying process, but is hindered from this by a counterforce, which counterforce can be deactivated by the user as a result of the application of a negative pressure through the mouthpiece of the hand-held device and furthermore enables a displacement of the cartridge into the dispensing position even without an application of negative pressure through the mouthpiece.

PRIOR ART

Hand-held devices for metered dispensing of sprayable substances are already known in various embodiments. For example, reference is made to WO 2009/037085 A1. Such hand-held devices are used in particular in medical aerosol therapy for the treatment of diseases of the respiratory tract. The pressurized cartridge held in the housing contains the medicament to be inhaled, wherein an axial movement of the cartridge relative to the housing is required to release or to expel the inhaler medicament.

In this connection, designs are further known in which, as in the aforesaid prior art, the cartridge is acted upon directly by hand, thus in particular in the base region of the cartridge, for movement relative to the housing. This manual triggering proves to be problematical in some patients. In addition, in order to achieve a correct inhalation, a pressing down of the cartridge in the housing to trigger the spray process must be performed at the same time is sucking in via the mouthpiece of the hand-held device.

In order to counter this problem, further solutions are known in which the triggering of the dispensing spray process is achieved as a result of the application of a negative pressure by sucking in via the mouthpiece of the hand-held device. To this end, the cartridge is previously brought into a ready-to-dispense position in which the cartridge is pre-tensioned in the direction of the dispensing spray position under the action of a spring. Such a configuration is known, for example, from U.S. Pat. No. 5,447,150 A. In this case, the cartridge in the housing is guided initially and substantially in a sealed chamber so that as a result of the initially performed displacement of the cartridge into the ready-to-dispense position, a compression of the air in the chamber is achieved in the direction of displacement upstream of the cartridge. The increasing air pressure produces a resistance load, which prevents the actuation of the valve spring-loaded in the cartridge to trigger the spray process. With the onset of a negative pressure application through the mouthpiece as a result of sucking in by the user, a further provided valve flap is moved by means of which a valve opening is released, wherein the air compressed in the previously described chamber is released. Due to the spring still acting on the cartridge, the cartridge is moved further into the dispensing spray position at this moment with accompanying opening of the spray valve and ejection of the substance into the suction stream.

Known from EP 414 536 A2 is a hand-held device for the metered dispensing of sprayable substances, in which a rocker part is arranged directly underneath a lower end face of a substance container, and can move another part that interacts with the valve flap while pressing down back into an original position given a return movement of the substance container. Also provided is a switch part inserted into an opening of the housing, which can be used to manually cancel the negative pressure block, i.e., without suction being required. The opening is occupied by the switch in both possible positions of the switch.

Known from EP 490 797 B1 is a hand-held device for dispensing sprayable substances, in which the cartridge itself is not displaced for dispensing, but rather a carriage arranged underneath the cartridge is activated by a user of the cartridge valve upon suction activation.

SUMMARY OF THE INVENTION

Proceeding from a prior art according to EP 0 414 536 A2, the invention deals with the object of configuring a hand-held device of the type in question, in particular as functionally reliable as possible.

This object is achieved in the subject matter of claim 1, wherein emphasis is placed on the valve flap being arranged underneath a first air-permeable housing base of the housing in the direction of movement of the cartridge from the rest position into the spray position, and on the housing base separating a chamber accommodating the valve flap to the mouthpiece.

As a result of the proposed configuration, the cartridge is held in its ready-to-dispense position by purely mechanical means and is thus initially prevented from further displacement into the dispensing spray position. This results in a particularly reliable configuration. There is no need for any expensive sealing of the cartridge surroundings, as is known from the prior art, which can also contribute to an advantageous manufacturability. With the usual, possibly frequent application of the hand-held device, leaks can occur in a region to be sealed, which adversely influence the functional safety of the hand-held device and furthermore can possibly influence the inhalation result.

The mechanical block can be brought about by an indirect or also direct mechanical support of the cartridge on the valve flap. Thus, the mechanical block can furthermore form an element which is placed in the displacement path of the cartridge relative to the housing to prevent further displacement of the cartridge beyond the ready-to-dispense position into the spray position. As a result of the application of negative pressure via the mouthpiece of the hand-held device, the valve flap is moved, for example, pivotally displaced, in such a manner that the mechanical block coupled therewith releases the displacement path of the cartridge as far as the spray position.

The direction of movement of the cartridge relative to the housing accommodating the cartridge is preferably linear, further preferably in the same direction of movement of the cartridge valve provided inside the cartridge for spray dispensing of the substance located in the cartridge. Furthermore, during the usual handling of the hand-held device in the course of an inhalation process in which handling the cartridge is aligned substantially oriented at least along a vertical axis, the valve flap is arranged in a base region of the housing substantially assigned to the mouthpiece of the housing.

In the direction of movement of the cartridge from the rest position into the spray position, the valve flap is arranged underneath a first air-permeable housing base. This first air-permeable housing base separates a chamber accommodating the valve flap from the mouthpiece and/or the air channel adjoining the mouthpiece. The air permeability of the first housing base is at least so extensive that a usual quantity of air can flow through the first housing base in the course of sucking in via the mouthpiece.

A specific release of the cartridge, i.e. a specific displacement of the cartridge from the ready-to-dispense position into the dispensing position can be achieved, for example, for test and/or diagnostic purposes without an application of negative pressure being made by the user via the mouthpiece. The mouth comprising the mouthpiece under application of negative pressure does not allow an examination and optionally a photographing, for example, of a spray pattern or does not allow this to a sufficient extent. For this purpose, an alternative release can be performed.

Thus, according to a further possible solution of the object, the focus can be on the fact that the housing has an opening formed additionally to the mouthpiece through which a release part can be introduced into the interior of the housing to deactivate the counterforce, that the opening enables a movement of the release part to act on a release carriage arranged inside the housing, and that a valve flap can be moved by the release carriage.

For this purpose, a separate opening can be provided in the housing. Alternatively, an opening provided in any case, in particular for carrying out the inhalation process and/or an opening necessary for displacement of the cartridge from the ready-to-dispense position into the dispensing position via an application of negative pressure can be used.

Through the opening a release part can grip into the interior of the housing in such a manner that after displacement of the cartridge into the ready-to-dispense position by means of the release part, the counterforce holding the cartridge in this ready-to-dispense position can be overcome so that a displacement of the cartridge into the dispensing position and thus a dispensing spray burst can be achieved.

As a result of this configuration, a spray burst can be delivered without an application of negative pressure being made via the mouthpiece. The spray burst expelled during this release via the release part via the mouthpiece can be analyzed in this way, measured and/or photographed.

In a further embodiment, the opening through which the release part can be inserted can be closed in the non-usage position of the hand-held device. Thus, in a further preferred embodiment, the opening can only be exposed for use in the course of the displacement of the cartridge from a base position into the ready-to-dispense position.

For manual cancelling of the counterforce, a tool (release part) which must be specifically and intentionally introduced through the opening is required. This prevents any unintentional release. Also preferably no features are provided on the housing, for example, in the form of a separate button or the like, which could bring about a manual triggering by the user.

The housing can have a spray nozzle from which the substances exits in the spray position of the cartridge. The spray nozzle of the housing is fluidically connected to a dispensing channel of the cartridge in the usage or ready position of the hand-held device. Via the spray nozzle during the dispensing spray process the substance stored in the cartridge is dispensed in a metered fashion into the air channel leading to the mouthpiece or oriented directly into the region of the mouthpiece.

According to a preferred embodiment, the first housing base can be formed underneath the spray nozzle, this being substantially with reference to the direction of movement of the cartridge from the rest position into the spray position.

Also the first housing base can be formed as part of a lower wall of the air channel, thus a relevant part of the lower channel wall beyond the mouthpiece in the direction of the housing interior.

The first housing base has at least one air passage, but optionally also a plurality of air passages, wherein according to a preferred embodiment one or each of the air passages in the first housing base is configured to be smaller than the valve flap. Accordingly, opening areas are obtained in the region of the air passages which are selected to be smaller in their extension than the relative extension dimensions of the valve flap. Thus, it is ensured that the valve flap cannot enter into the region of the air channel and via this into the region of the mouthpiece. Accordingly, it is ensured that a valve flap which is possibly released from the holder during use of the hand-held device, for example, due to damage does not enter into the air channel and the mouthpiece, and can be breathed in via this. On the contrary the valve flap is captive in the part chamber possibly established below the first housing base.

The mechanical block of the movement of the cartridge which can be cancelled via the valve flap can, according to one embodiment, be given by a stop. This stop acts indirectly or directly together with a section of the cartridge, in particular the cartridge housing.

The stop can be slidingly displaceable, in particular linearly displaceable, to release the movement of the cartridge in the direction of the spray position. Furthermore, the stop with the valve flap can be pivotable to release the cartridge movement. The pivot axis of the stop can in this case at the same time be the pivot axis of the valve flap. In this case, the geometrical pivot axis of the valve flap and/or the stop can be transversely directed to the direction of movement of the cartridge.

In a further embodiment, the cartridge can act upon a stop part. Via this stop part, the cartridge can be supported indirectly on the stop of the valve flap in the ready-to-dispense position. The stop part can be a separate part with respect to the cartridge, which furthermore can be assigned accordingly to the cartridge.

The valve flap itself can comprise the stop, thus for example, as a result a one-piece, optionally moreover, uniform-material configuration of valve flap and stop. Thus, the valve flap with the stop can, for example, be a plastic injection-moulded part. The stop part of the cartridge is accordingly configured to interact with the valve flap or with the stop of the valve flap.

The cartridge-side stop part can have at least one stop extension which passes through the air channel of the hand-held device to cooperate with the stop on the valve flap side. Such a stop extension can, for example, be configured to be pin-like. In a further embodiment, a plurality of, thus in particular two such stop extensions can be provided, which can be arranged to run on both sides of the housing-side spray nozzle. In the case of two stop extensions, for example, these can cooperate with a corresponding number of stops which are movement-coupled. In a preferred embodiment, both stop extensions cooperate with only one flap-side stop.

The stop can be connected fixedly to the valve flap. Alternatively with regard to the pivotability, a stop which is movement-connected to the valve flap can be provided, which however is provided rotatably about the longitudinal axis of the stop relative to the valve flap or to holder regions for the stop. Thus the stop can, for example, be rod- or roll-shaped with an axis of rotation running parallel to the pivot axis of the valve flap and the stop. This results in a further improved functionality, in particular in the course of the valve flap pivoting during sucking in via the mouthpiece so that in the course of the pivoting, the stop thus configured can pivot out from the support position for the stop part of the cartridge in an improved manner.

The stop part can, according to a further embodiment for example, be part of a counter mechanism which is moved by the cartridge during movement into the spray position. Such a counter mechanism is known from the initially cited literature WO 2009/037085 A1. The counter mechanism can be arranged substantially in the region between cartridge and air channel surrounding the dispensing valve tube of the cartridge, wherein the counter mechanism is supported with one section on a housing section, for relative displacement between components of the counter mechanism in the course of the movement of the cartridge from the rest position into the spray position. By this means the inhalation process is detected. The user can read off, for example, the number of spray bursts at least still provided via a viewing window or the like.

According to one embodiment, a part of the counter mechanism can be co-displaced over the overall possible displacement path of the cartridge in the housing. This part region of the counter mechanism is accordingly substantially movement-coupled to the cartridge and according to a possible embodiment, carries the aforementioned stop part. The stop part accordingly provides an extension of the cartridge acting on the stop via the counter mechanism.

In a further embodiment, the housing can have a support part for the spring which can be acted upon relative to the cartridge to tension the spring acting on the cartridge. In a further embodiment, the support part can be part of the housing, which can be arranged slidingly displaceably with respect to a fixed part of the housing in the direction of movement of the cartridge. Furthermore, in this respect a telescopic arrangement of the support part and the fixed housing part can be given.

In a further embodiment, the support part can surround the cartridge in a pot-like manner, wherein the relevant pot base can overlay the upwardly pointing cartridge base during usual usage of the hand-held device. The pot base of the support part can in this case provide the counterbearing for the spring acting on the cartridge, in particular on the cartridge base.

In an advantageous manner, the hand-held device can have a mouthpiece closure cap. This can also preferably be arranged undetachably on the housing. This affords the further possibility of movement-coupling the mouthpiece closure cap with the support part acting on the cartridge via the spring. Accordingly, a displacement of the mouthpiece closure cap from the position covering and protecting the mouthpiece into the position releasing the mouthpiece and back brings about a movement-coupled linear displacement of the support part. Thus, during a displacement of the mouthpiece closure cap into a position releasing the mouthpiece, a linear displacement of the support part bringing the cartridge from the rest position into the ready-to-dispense position via the spring can result. With the return of the closure cap into the position covering the mouthpiece, a corresponding back-displacement of the support part into a base position is achieved, with a corresponding reduction of the spring force acting on the cartridge. In one possible embodiment, the spring force acting on the cartridge in such a base position is at least approximately zero.

The cartridge and the counter mechanism substantially movement-coupled to this are in particular displaced back into the rest position starting from the spray position, but optionally also starting from the ready-to-dispense position, via the cartridge-side valve spring. Thus, further according to a possible embodiment, this cartridge-side valve spring can already be brought into a pre-tension in the ready-to-dispense position.

The movement coupling between mouthpiece closure cap and support part can be given by an eccentric application of a cap extension. Via the eccentric, a preferred pivoting movement of the closure cap can be translated into a translational movement of the support part. Also according to one possible embodiment, a controlled back-displacement of the support part into the rest position can be accomplished via the eccentric application.

During a movement of the mouthpiece closure cap into an open position, the movement coupling can result in the tensioning of the spring between the support part and the cartridge, this being due in particular, according to one embodiment, to the fact that as a result of the stop stemming into the movement direction of the cartridge, the amount of displacement of the cartridge in the movement direction is smaller than the corresponding amount of displacement of the support part. This results in a tensioning of the spring which is released with continued pivoting of the stop in the course of the sucking in via the mouthpiece, for further displacement of the cartridge (and optionally the counter mechanism) in the direction of movement, wherein under housing-side support of the cartridge-side valve tube, the cartridge-internal valve is opened contrary to the valve spring force and a spray burst is dispensed.

The spring force acting on the cartridge in the spray position via the spring acting between cartridge and housing, for example, support part is in this case selected to be greater than the counterforce to be applied by the cartridge-side valve spring.

In a further embodiment the release part can be configured in the form of a tappet or a pin to release the cartridge displacement from the ready-to-dispense position into the dispensing position without application of a negative pressure via the mouthpiece. This release part is preferably not part of the hand-held device issued to the user.

The release part can be movable to act on a release carriage arranged inside the housing. The release carriage can be accommodated slidingly displaceably in the housing, optionally pre-tensioned into a base position under spring loading. Via the release part introduced through the opening, the release carriage can be displaced out from a base position into a release position, this possibly by overcoming a restoring spring force, in which release position the counterforce can be deactivated when the cartridge stays in the ready-to-dispense position.

In a further embodiment, as mentioned, a valve flap can be provided which is movable under negative pressure. By means of the valve flap movement, for example, a mechanical block of the displacement of the cartridge from the ready-to-dispense position into the dispensing position can be cancelled.

In connection with a release without application of a negative pressure via the mouthpiece, according to a further preferred embodiment it can be provided that the valve flap is movable by the release carriage. Accordingly, the valve flap can be designed for pivoting by means of application of a negative pressure during normal use of the hand-held device and for pivoting directly via the release part or indirectly via the release carriage. The release carriage can in this case act directly on the valve flap so that a displacement of the release carriage can result in a corresponding displacement of the valve flap.

The valve flap can furthermore, alternatively to cancelling a mechanical block, open an air passage, in particular to reduce a counterforce holding the cartridge in the ready-to-dispense position.

BRIEF DESCRIPTION OF THE DRAWINGS

The invention is explained in detail hereinafter with reference to the appended drawings, which however merely show exemplary embodiments. A part which is only explained in relation to one of the exemplary embodiments and which is not replaced by another part in a further exemplary embodiment as a result of the particular feature established there is therefore described for this further exemplary embodiment as a part which is provided in any case. In the drawings:

FIG. 1 shows the hand-held device in perspective view with mouthpiece closed by a closure cap;

FIG. 2 shows a front view towards the hand-held device;

FIG. 3 shows the section along the line III-III in FIG. 2 through a hand-held device of a first embodiment, relating to the rest position of a cartridge accommodated in the hand-held device housing;

FIG. 4 shows a schematic side view towards the hand-held device in the position according to FIG. 3;

FIG. 5 shows an enlarged view of region V in FIG. 4;

FIG. 6 shows a sectional view substantially corresponding to FIG. 3 but relating to an intermediate position in the course of a pivoting movement of the mouthpiece closure cap;

FIG. 7 shows a following diagram to FIG. 6 relating to a ready-to-dispense position of the cartridge with a mouthpiece closure cap in the open position;

FIG. 8 shows a diagram corresponding to FIG. 4 but relating to the situation according to FIG. 7;

FIG. 9 shows an enlarged view of region IX in FIG. 8;

FIG. 14 shows a sectional view corresponding to FIG. 12 relating to the situation according to FIG. 10;

FIG. 15 shows the region XV in FIG. 14, relating to an alternative solution;

DESCRIPTION OF THE EMBODIMENTS

Figure 10:
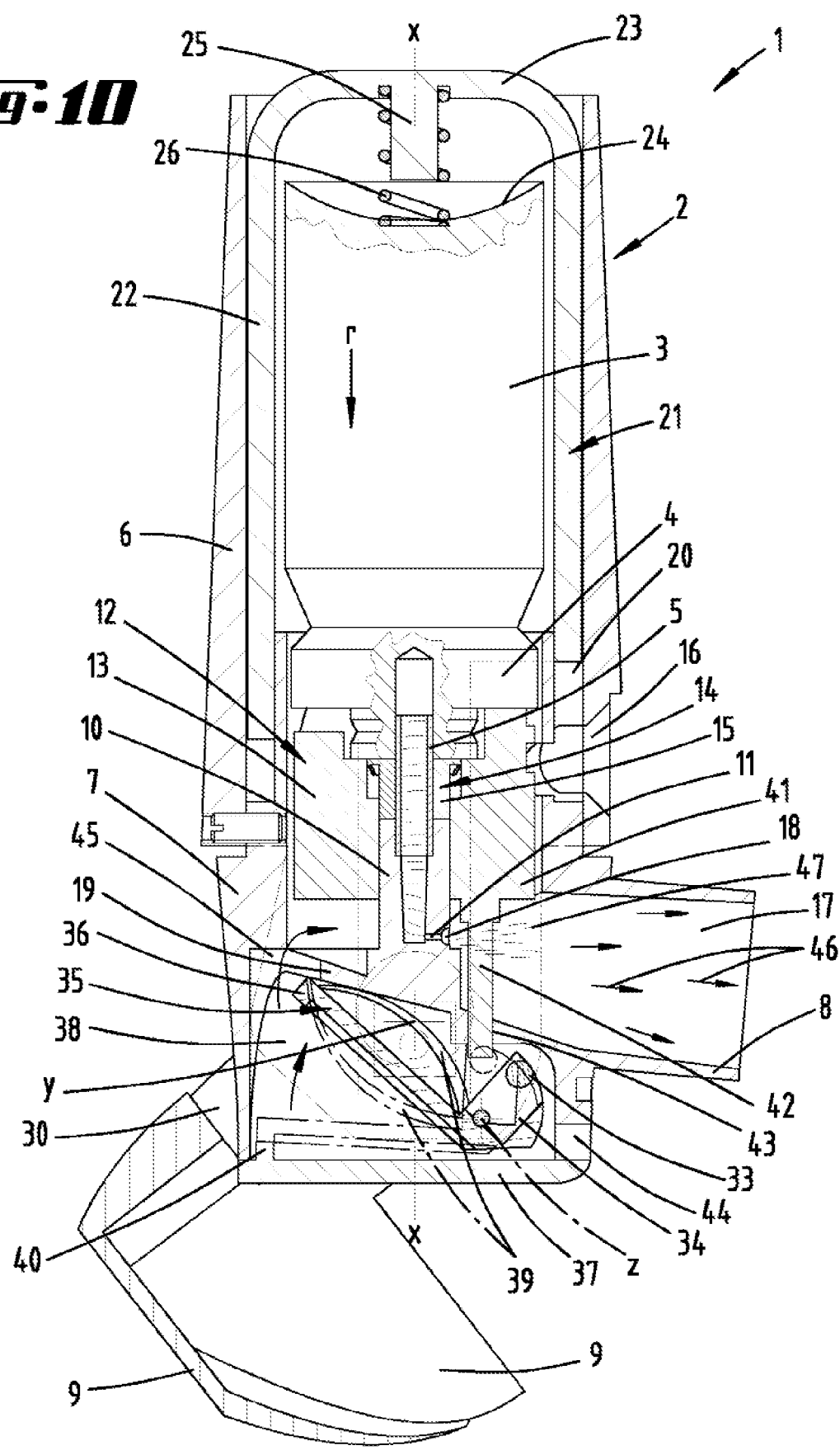
FIG. 10 shows a following diagram to FIG. 7, relating to the situation at the instant of a spray expulsion of a substance located in the cartridge accompanying an intake process.

A hand-held device 1 for the metered dispensing of sprayable substances, in particular of inhaler medicaments is shown and described, initially with reference to FIG. 1.

The hand-held device 1 has a housing 2 in which a cartridge 3 containing the sprayable substance is inserted. The cartridge 3 is axially displaceable in the housing 2 with reference to an axis x running in the longitudinal direction of the cartridge 3, which substantially also represents the longitudinal axis of the hand-held device 1 overall.

In the usual manner the cartridge head 4 has a central valve tube 5 extending coaxially to the cartridge 3. Via the latter a substance dispensing is achieved by an axial relative movement between cartridge 3 and housing 2.

The housing 2 can, as shown, be configured to be substantially divided in two, so further consisting of two annular parts 6 and 7 arranged one above the other in the axial direction, of which the upper annular part 6 in the diagrammatic views, which also substantially correspond to the usual alignment of the hand-held device 1 in use, is configured to be shaft-like and the lower annular part 7 has a mouthpiece 8 aligned approximately transversely to the shaft extension. The latter can be closed by a mouthpiece closure cap 9 when the hand-held device 1 is not being used.

The valve tube 5 of the cartridge 3 is supported in an assigned tubular support section 10 inside the lower annular part 7, this being inside the housing 2 surrounding the cartridge 3 with axial mobility of the cartridge 3.

The support section 10 formed inside the lower housing annular part 7 and holding the valve tube 5 of the cartridge 3 in a clamping manner is provided with a reduced-diameter flow channel 11 with respect to a section holding the valve tube end, which flow channel is in fluidic communication with the valve tube 5, wherein the end of the flow channel 11 facing away from the valve tube 5 points in the direction of the mouthpiece 8.

In the depicted exemplary embodiments, the two annular parts 6 and 7 are connected to one another in a pluggable manner. Alternatively however, the two parts can also be connected to one another via a thread, for example, via a coarse thread with a high pitch.

The arrangement of the cartridge 3 in the housing 2 is further selected so that the cartridge head 4 in the housing 2 is placed approximately at the height of the connection region between the annular part 6 and the annular part 7.

Located centrally underneath the opening-side front wall of the cartridge 3 in overlap with the cartridge valve tube 5 is a counter mechanism 12 or step-by-step indexing mechanism. This is used to register and display the dispensing actuations performed, this as a function of the executed opening strokes of the cartridge 3.

Such a counter mechanism is known from the initially mentioned WO 2009/037085 A1. With reference, for example, to the diagram in FIG. 3 the relationship with the subject matter described in the afore-mentioned WO documents can be identified possibly with a view to a schematically depicted housing 13 and a step-by-step indexing finger star 14. In this connection, it should be identified overall that the step-by-step indexing finger star 14 is supported via a hub 15 on the support section 10 of the lower annular part 7 whilst the counter mechanism 12 in particular comes to abut via the housing 13 to the facing front face of the cartridge head 4. Via a viewing window 16 the scale ring of the counter mechanism 12 can be seen in one section, in which section preferably the number of inhaler doses at least still present in the cartridge 3 is indicated.

In the first exemplary embodiment shown in FIGS. 1 to 11 the viewing window 16 is assigned to the front side of the hand-held device 1 facing the mouthpiece 8 and in the non-usage position for example according to FIG. 3 can be covered by the closure cap 9.

Alternatively as shown by reference to the second exemplary embodiment shown in FIGS. 12 to 15, the viewing window 16 can be provided towards the rear, i.e. on the side facing away from the mouthpiece 8. The counter value can be read off here independently of a usage position of the hand-held device 1 overall, accordingly also independently of a closure cap position.

The flow channel 11 passing through the support section 10 opens into an air channel 17 which extends substantially inside the lower annular part 7, surrounding the support section 10 and opens into the mouthpiece 8. The free end of the flow channel 11 opening into the air channel 17 forms a spray nozzle 18.

The air channel 17 is delimited downwards, accordingly pointing away from the counter mechanism 12 by a first housing base 19, which first housing base 19 in the depicted exemplary embodiment substantially goes over into a lower boundary wall of the mouthpiece 8 with reference to the diagrams.

An annular chamber 20 is formed between the outer wall of the cartridge 3 and the inner wall of the upper annular part 6 of the housing 2. A pot-shaped support part 21 with its circumferential wall 22 running concentric to the axis x engages into this annular chamber. The pot base of the support part 21 extends in the manner of a dome-like cover 23 over the cartridge 3, wherein a spacing a when viewed in the axial direction remains between the cartridge base 24 and the facing underside of the cover 23.

On the underside of the cover 23 a mandrel 25 is moulded on in the centre, accommodating the axis x centrally. This is surrounded by a spring 26 in the form of a cylinder compression spring, which is supported at one end on the cover 23 of the support part 21 and at the other end on the facing cartridge base 24.

In the rest position of the cartridge 3 shown for example with reference to the first exemplary embodiment in FIG. 3, which corresponds to the non-usage position, in a preferred embodiment the spring 26 rests on the cartridge base 24 without applying force. The spring 26 accordingly does not bring about any or no significant loading of the cartridge 3 in its direction of movement r. On the contrary, the cartridge 3 is held in its usual base position, in which base position the cartridge 3 is urged with respect to the valve tube 5 held in the support section 10 along the axis x with reference to the diagrams upwards in the direction of the support part cover 23, this as a result of a corresponding stop-limited spring resetting of a valve spring provided inside the cartridge 3 in the region of the valve tube 5.

The support part 21 is slidingly displaceable linearly along the axis x in the annular chamber 20. To this end, the support part 21 in the depicted exemplary embodiment with reference to a cross-section transversely to the x axis has two diametrically oppositely arranged sections 27 formed preferably in one piece with the wall 22 of the same material, which extend sections of the wall 22 in a tab-like manner beyond the edge of the wall 22 facing away from the cover 23. In the rest position shown in FIG. 3, the sections 27 extend approximately into a projection to the first housing base 19 when viewed transversely to the axis x.

In the respective end region of the sections 27, a window-like cut-out or a window-like recess 28 is formed in which an eccentric cam 29 of the mouthpiece closure cap 9 engages.

To this end, the mouthpiece closure cap 9 has respectively one cantilever-type cap extension 30 on both sides of the axis x viewed onto the mouthpiece opening, in each of which one eccentric cam 29 is arranged. The eccentric cam 29 engages in the recess 29 of the assigned support part section 27.

The geometrical axis of rotation y of the mouthpiece closure cap 9 is accomplished as a result of cooperation of respectively outwardly pointing axial stumps 31 on the cap extensions 30, which engage in correspondingly positioned and dimensioned bore-like axial receptacles 32 in the housing 2, in particular of the upper annular part 6.

As can be seen for example in FIG. 5, an eccentric offset of the eccentric cam 29 with respect to the axis of rotation y is obtained which axis of rotation y in the depicted exemplary embodiment intersects the x axis in a traversing manner.

As a result of the previously described configuration, an eccentric action of the support part 21 via the cap extensions 30 is achieved with pivoting-up of the mouthpiece closure cap 9. The pivoting-up of the mouthpiece closure cap 9 by pivoting the same downwards with reference to the diagrams results in a linear lowering of the support part 21.

The linear lowering of the support part 21 brings about via the spring 26 a limited linear movement of the cartridge 3 downwards in the direction of the support section 10, wherein as a result of the supporting of the valve tube 5 on the support section 10, the valve tube 5 dips in the direction of the cartridge interior against the force of the cartridge-side spring. A dragging entrainment of the cartridge 3 into a position in which the cartridge-internal valve opens, accordingly a sufficiently large relative displacement of cartridge 3 and valve tube 5 is achieved, is initially prevented as a result of a mechanical block S (see FIG. 7).

The mechanical block S prevents the cartridge 3 from any further displacement and holds the cartridge 3 in a ready-to-dispense position.

In the depicted exemplary embodiment, the mechanical block S is given by a stop 33. The stop 33 according to the depicted embodiment is configured to be pin-like with a circular disk-shaped cross-section, wherein the rod longitudinal axis runs parallel to the axis of rotation of the mouthpiece closure cap 9.

In the depicted exemplary embodiment, the pin-shaped stop 33 is held at both ends in a cantilever 34 of a provided valve flap 35.

The valve flap 35 is held pivotably about a pivot axis z in the lower annular part 7, which pivot axis z runs in the rest position of the valve flap 35 substantially underneath the stop 33 with reference to the movement direction r of the cartridge 3.

With reference to a cross-section according to FIG. 3, the flap base 36 extends approximately in right-angle alignment to the cantilever 34.

Overall the valve flap 35 with its cantilever 34 and the stop 34 when viewed in the direction of movement r of the cartridge 3, is arranged underneath the first housing base 19, in particular in a flap chamber 38 delimited between the first housing base 19 and a second housing base 37 inside the lower annular part 7.

The valve flap 35 can be a plastic injection-moulded part. This affords the advantage of the direct formation of a restoring arm 39 acting in a spring-like manner on the valve flap 35. This is supported on the underside on the first housing base 19 and urges the valve flap 35 into its base position according to FIG. 3 in which this rests on the second housing base 37 or here abuts against a support block 40.

The stop 33 or the mechanical block S in particular in the ready-to-dispense position according to FIG. 7 cooperates with a stop part 41 of the cartridge 3. This stop part 41 can, as also shown, be part of a counter mechanism 12, for example of the housing 13 (see also FIG. 11). The stop part 41 has for direct cooperation with the stop 33, a stop extension 42, which in a pin-like manner passes through the air channel 17 in alignment of the axis x traversing the first housing base 19 in the region of a correspondingly formed and preferably cross-sectionally adapted breakthrough 43.

Figure 11:
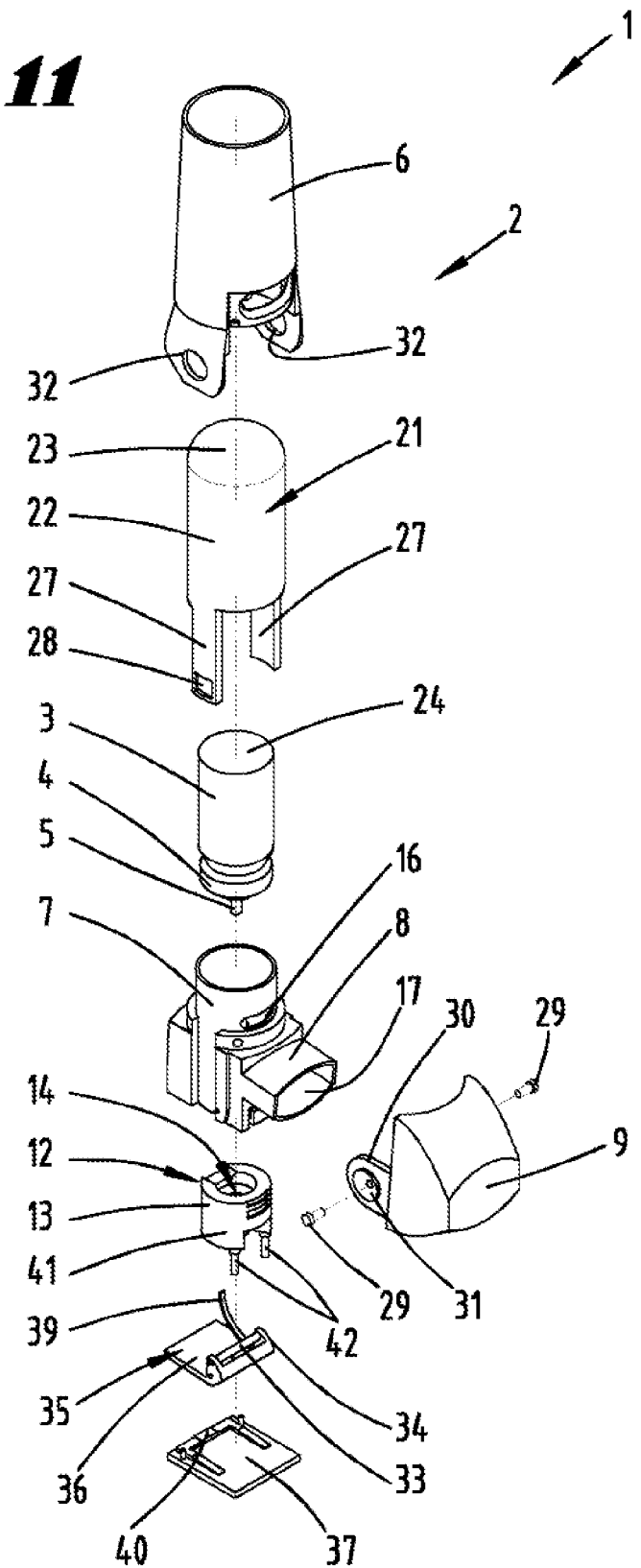
FIG. 11 shows the hand-held device in a perspective exploded view.

As can be seen in particular from the diagram in FIG. 11, two such stop extensions 42 are provided which, viewed towards the mouthpiece opening surface extend on both sides of the x axis and jointly cooperate with the stop 33.

In the ready-to-dispense position according to FIG. 7, the cartridge 3 is accordingly supported via the counter mechanism 12 and over this via the stop extensions 42 on the flap-side stop 33. The displacement of the cartridge 3 along the x axis is thereby limited whereas via the eccentric action using the closure flap 9 the displacement path of the support path 21 is larger compared with the displacement path of the cartridge 3 in the movement direction r.

In FIG. 7 the base positions of support part 21 and cartridge 3 are each shown by dashed lines. It can be seen that the linear displacement distance b of the support part 21 out from the rest position into the ready-to-dispense position corresponds to a multiple of the displacement distance c of the cartridge 3 from the rest position into the ready-to-dispense position. Thus, the displacement distance b of the support part 21 can approximately correspond to 1.5 to 3 times, further approximately 2 to 2.5 times the cartridge-side displacement distance c.

The difference between the displacement distances b and c is taken up as a result of the compression of the spring 26 and a relative displacement of the valve tube 5 to the cartridge 3. As a result of the support of the valve tube 5 on the support section 10 and the displacement of the cartridge 3 in the movement direction 5, a dipping-in of the valve tube 5 over a displacement distance d is obtained here against the cartridge-internal spring. The valve tube 5 is introduced so far here that the valve provided in the cartridge 3 is just ahead of triggering.

In order to bring the cartridge 3 into the spray position according to FIG. 10, it is necessary to cancel the mechanical block S. This cancelling is accomplished as a result of an application of negative pressure in the course of sucking in air by the user. The user encloses the mouthpiece 8 with his lips and breathes in deeply in the usual manner as in the hand-held devices of the type in question which are known from the prior art. The sucked-in air is sucked in via an inflow opening 44 which passes through the relevant wall in the annular part 7 below the mouthpiece 8 and leads into the flap chamber 38 and is guided via at least one air passage 45 in the first accordingly air-permeable housing base 19 into the air channel 17. As a result of the negative pressure established here in the flap chamber 39 at the top of the valve flap 35, the valve flap 35 is sucked in and pivoted about the pivot axis z, this in the clockwise direction with reference to the diagrams, further accordingly in the direction of the underside of the first housing base 19.

The pivoting is accomplished against the restoring force of the restoring arm 39 which is accordingly designed to be weak, in order to be overcome merely via the negative pressure. However, the restoring arm 39 is set so strongly in relation to its restoring capacity that this alone ensures a restoring movement of the valve flap 35 into the base position.

In the course of the flap pivoting movement from the ready-to-dispense position into the spray position, in the embodiment shown the restoring arm 39 goes over via a dead point position (compare diagram in FIG. 10).

As a result of the pivoting displacement of the valve flap 35, a pivoting down of the stop 33 is obtained. In this case, an arrangement of the stop 33 which is preferably freely rotatable about the rod axis is advantageous since an improved downward pivoting can be accomplished despite application of force via the stop extension 42.

The stop extension 42 is as a result released almost abruptly. The corresponding support for the cartridge 3 is lacking, and this is forcibly displaced into the spray position according to FIG. 10 as a result of the initially different displacement distances b and c of the tensioned spring 26. The force of the cartridge-internal spring is further overcome and the cartridge-internal valve is opened as a result of the corresponding relative displacement of cartridge 3 and valve tube 5. The substance stored in the cartridge 3 flows in a metered fashion through the flow channel 11 and enters via the spray nozzle 18 into the air channel 17 and further into the intake air as a result of the sucking process triggering the spray ejection (shown by the arrow 46). The spray burst is provided with the reference number 47.

With the end of the inhalation process and accompanying termination of the sucking-in process, as a result of the lack of application of negative pressure the valve flap 35 falls back whilst pivoting about its axis of rotation z. After this, the stop 33 can initially come laterally against one or both stop extensions 42 so that final restoring of the valve flap 35 can only be achieved again upon reaching the base position in which the valve flap 9 is pivoted via the mouthpiece 8.

With the back-pivoting of the closure cap 9 to close the mouthpiece 8, the dragging entrainment via the eccentric cam 29 is cancelled. A usual resetting of the cartridge 3 is accomplished and via the spring 26 of the support part 21 into the base position as a result of release of tension of the cartridge-side valve spring. Alternatively the resetting in particular of the support part 21 can also be accomplished via the eccentric cam 29.

The diagrams in FIGS. 12 to 15 show a second embodiments of a hand-held device 1 according to the invention. With regard to the external design and furthermore also the basic function with regard to the handling of the hand-held device 1 for inhalation, the hand-held device 1 of the second embodiment substantially corresponds to that of the previously described first embodiment.

Thus, here also a cartridge 3 is accommodated in a support part 21, wherein a spring 26 is provided between the cartridge 3 and the support part cover 23.

The valve tube 5 is accommodated in a support section 10 of the housing 2. Here also a counter mechanism 12 assigned to the cartridge head 4 is provided, on which as in the previously described exemplary embodiment, a finger-like extension 42 is rigidly connected.

Here also in this second embodiment as a result of pivoting the mouthpiece closure cap 9 downwards, the hand-held device 1 can be brought into a ready-to-dispense position in which the cartridge 3 is supported via the counter mechanism 12 and over this via the stop extension or extension 42 on a stop 33.

On the underside of the first housing base 19, a valve flap 35 is also provided in the second exemplary embodiment in a valve chamber 38, which valve flap is mounted pivotably about a geometric pivot axis z in the flap chamber 38.

In this embodiment the stop 33 is designed in the manner of a roller. This roller can, as is also preferred, be held rotatably on the valve flap 35 about a geometrical axis running parallel to the pivot axis z of the valve flap 35.

As can be further identified in particular from the perspective diagram in FIG. 15, this roller-type stop 33 can have a central enlarged-diameter region 48 in the direction of longitudinal extension of the relevant geometrical axis of rotation. This diameter dimension can, for example, correspond to 1.5 to 2.5 times the diameter dimension of the roller regions each forming a stop 33, which is established on both sides of the region 48 viewed in longitudinal extension.

Instead of a resilient restoring arm 39, such as is used in the previously described first embodiment, according to the second embodiment, a separate spring 49 can now be provided. Here, as is also shown, this can comprise a cylinder spring, further for example a metal cylinder compression spring.

Furthermore, on the underside of the support section 10, possibly at the same time forming at least a part of the first housing base 19, a docking part 50 can be provided. This can comprise at least one retaining pin 51 projecting into the flap chamber 38, on which one end of the spring 49 is held.

Figure 12:
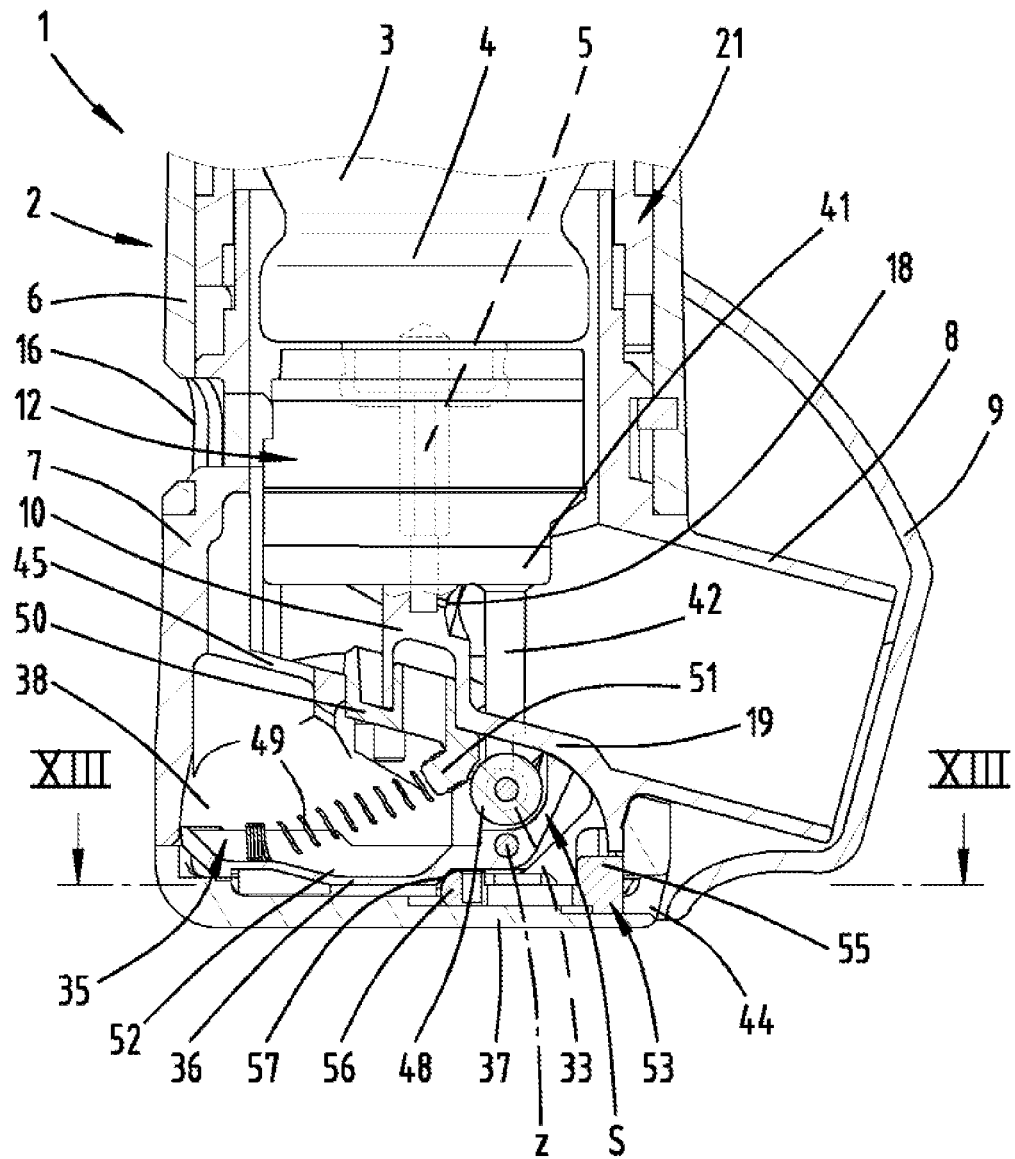
FIG. 12 shows in a sectional view according to FIG. 3 a section of a hand-held device in a second embodiment, relating to the rest position.
Figure 13:
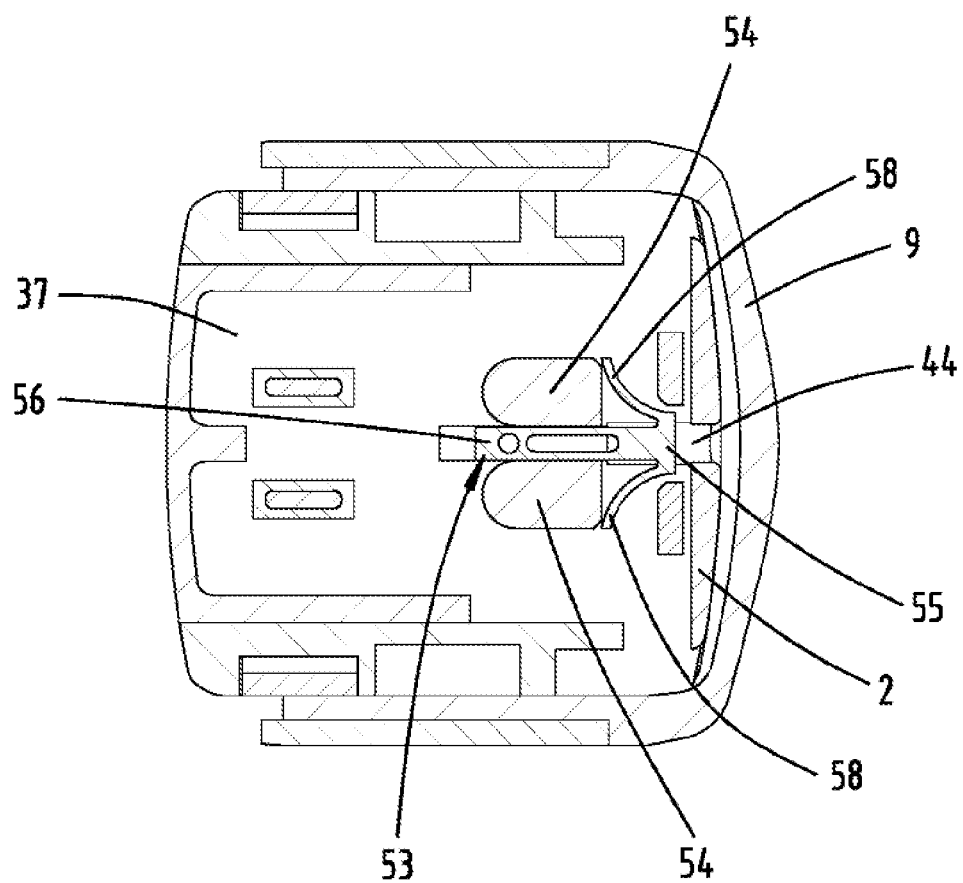
FIG. 13 shows the section along the line XIII-XIII in FIG. 12.
Figure 16:
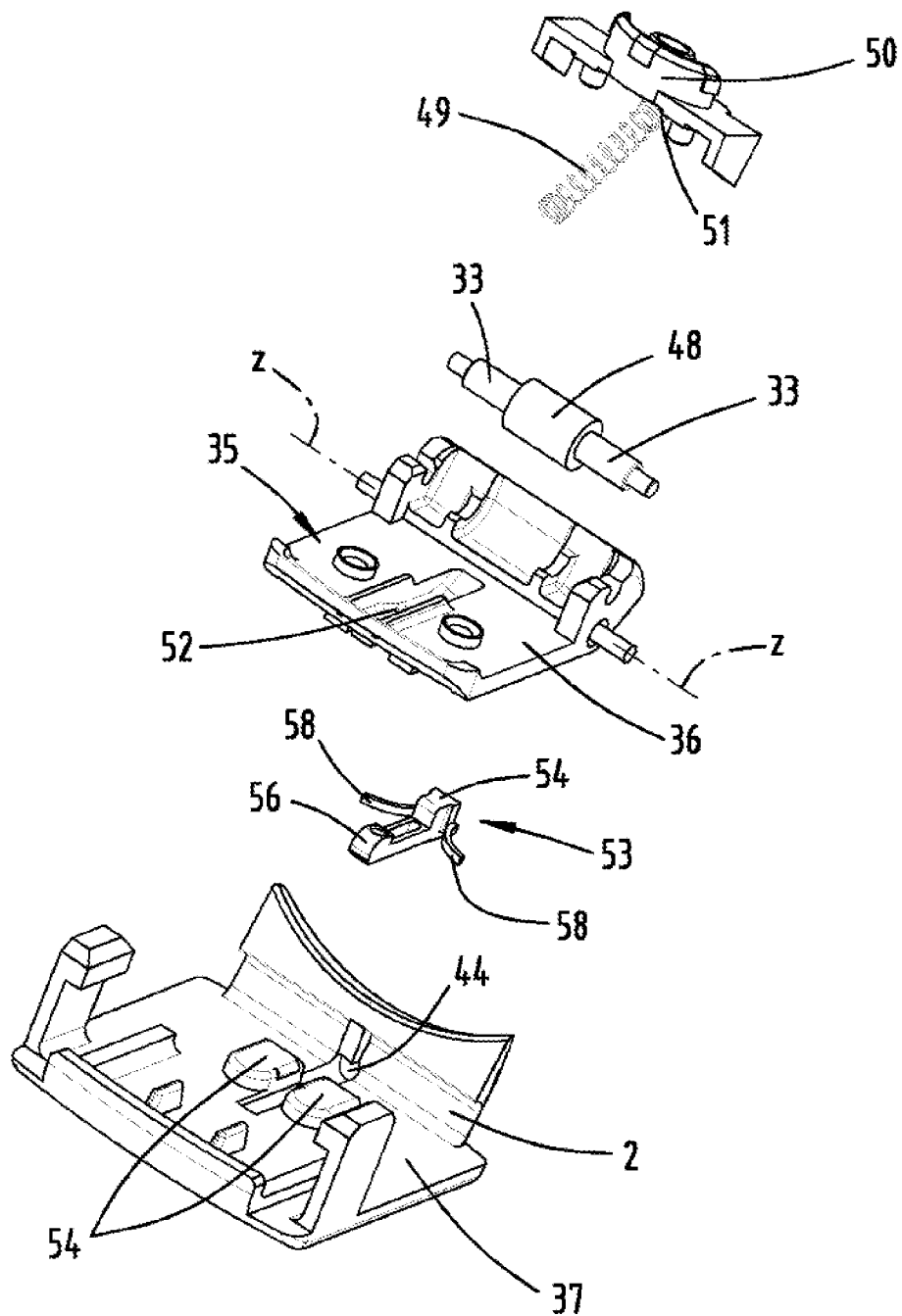
FIG. 16 shows an exploded perspective view of a partial region of the hand-held device of the second embodiment.

The free end of the spring 49 facing away from the retaining pin 51 acts on the valve flap 35 in such a manner that the valve flap 35 is loaded in the direction of its base position shown in FIG. 12.

This free end of the spring 49 can, as is also preferred and depicted, dip into a trough-like recess 52 of the valve flap 35.

In this embodiment also, a cancelling of the mechanical block S between the stop 33 and the stop extension 42 is required to bring the cartridge 3 into the spray position according to FIG. 14. This cancelling is here also accomplished as a result of an application of negative pressure in the course of a sucking in of air by the user via the mouthpiece 8.

The sucked-in air is here also sucked in via an inflow opening 44 provided underneath the mouthpiece 8 in the annular part 7 and guided via at least one air passage 45 in the first accordingly air-permeable housing base 19 into the air channel 17. As a result of the suction flow established here, optionally due to the negative pressure established at the top of the valve flap 35, the valve flap 35 is sucked in and pivoted about the pivot axis z into the position according to FIG. 4 against the restoring force of the spring 49.

The cylindrical spring 49 in the exemplary embodiment can in this case be subjected to a compression acting substantially in the longitudinal direction of the spring 49. Furthermore, as is also shown in FIG. 14, a bending of the spring 49 overall can be given from its stretched alignment.

When the suction air flow is terminated or the negative pressure loading which overcomes the spring force is fallen below, the valve flap 35 is displaced back into its initial position again according to FIG. 12 by means of the spring 49.

In addition, a preferably shoe-like release carriage 53 can be provided on the second housing base 37 and substantially assigned to the underside of the valve flap 35. This is preferably arranged slidingly displaceably on the second housing base 37 in a direction transverse to the alignment of the pivot axis z, here preferably when viewed in the displacement direction guided on both sides by guide blocks formed on the housing base 37.

Furthermore a release section 56 can be formed on an action section 55 facing the inflow opening 44 in the displacement direction opposite to the release carriage 53. In a base position according to FIG. 12 this can abut against a facing control surface 57 in the region of an underside of the valve flap 35 or be arranged facing this control surface 57.

As can be further identified in particular from the perspective view in FIG. 15, the release carriage 53, possibly formed of the same material and in one piece, can have one or two spring arms 58 by means of which the release carriage 53 is supported on a fixed housing part, thus for example on the front faces of the guide blocks 54. These front faces of the guide blocks 54 point substantially in the direction of the mouthpiece 8 so that the spring arms 58, substantially rooted in the region of the action section 55, can extend substantially between the guide blocks 54 and the wall section having the inflow opening 44.

The spring arms 58 are configured so that the release carriage 53 undergoes a spring loading in the direction of the base position according to FIG. 12.

Using the release carriage 53, in particular for test or adjustment purposes a triggering of a spray burst can be achieved without a user sucking in air via the mouthpiece 8. For this purpose a pin-like release part 59 can be guided through the inflow opening 44 provided in any case, by means of which by acting on the action section 55, the release carriage 53 is slidingly displaced against the restoring force of the spring arms 58. The release section 56 in this case cooperates with the control surface 57 of the valve flap 35 in such a manner that the valve flap 35 can reach into the position releasing the stop extension 42 according to FIG. 15 against the restoring force of the spring 49. In this way, a displacement of the cartridge 3 from the ready-to-dispense position into the dispensing position can be achieved and thus, for example, the spray pattern can be tested and possibly photographed.

A hand-held device, characterized in that the spray nozzle 18 delivers into an air channel 17 formed partially by the mouthpiece 8.

A hand-held device, characterized in that the first housing base 19 is formed underneath the spray nozzle 18.

A hand-held device, characterized in that the first housing base 19 is formed as part of a lower wall of the air channel 17.

A hand-held device, characterized in that one or each of the air passages 45 in the first housing base 19 is configured to be smaller than the valve flap 36.

A hand-held device, characterized in that the mechanical block S of the movement of the cartridge 3 is given by a stop 33.

A hand-held device, characterized in that the stop 33 with the valve flap 35 is pivotable to release the cartridge movement.

A hand-held device, characterized in that the cartridge 3 acts upon a stop part 41.

A hand-held device, characterized in that the valve flap 35 comprises the stop 33 and that the stop part 41 is configured to interact with the valve flap 35.

A hand-held device, characterized in that the stop part 41 has a stop extension 42 which passes through the air channel 17 of the hand-held device 1.

A hand-held device, characterized in that the stop part 41 is part of a counter mechanism 12 which is moved by the cartridge 3 during movement into the spray position.

A hand-held device, characterized in that the housing 2 has a support part 21 for the spring 26 which can be acted upon relative to the cartridge 3 to tension the spring 26.

A hand-held device, characterized in that the hand-held device 1 has a mouthpiece closure cap 9 and that the mouthpiece closure cap 9 is movement-coupled to the support part 21.

A hand-held device, characterized in that the movement coupling is given by an eccentric application of a cap extension 30.

A hand-held device, characterized in that during a movement of the mouthpiece closure cap 9 into an open position, the movement coupling results in a tensioning of the spring 26.

A hand-held device, characterized in that the housing 2 has an opening 44 formed additionally to the mouthpiece 8 through which a release part 59 can be introduced into the interior of the housing 2 to bring the counterforce out of action.

A hand-held device, characterized in that the release part 59 is a tappet.

A hand-held device, characterized in that the release part 59 is movable to act on a release carriage arranged inside the housing 2.

A hand-held device, characterized in that a valve flap 35 is provided which is movable by negative pressure.

A hand-held device, characterized in that the valve flap 35 is movable by the release carriage 53.

A hand-held device, characterized in that the valve flap 35 cancels a mechanical block of the cartridge 3 from the ready-to-dispense position into the release position.

All the disclosed features are (for themselves and also in combination with one another) essential to the invention. In the disclosure of the application, the disclosure content of the relevant/appended priority documents (copy of the prior application) is herewith included in its full content, also for the purpose of incorporating features of these documents in claims of the present application. The subclaims characterize, even without the features of a referenced claim, with their features independently inventive further developments of the prior art, in particular to make divisional applications on the basis of these claims. The invention specified in each claim can additionally comprise one or more of the features specified in the preceding description, in particular provided with reference numbers and/or given in the reference list. The invention also relates to design forms in which individual ones of the features mentioned in the preceding description are not implemented, in particular insofar as they are identifiably dispensable for the respective usage purpose or can be replaced by other means having technically the same effect.

REFERENCE LIST

1 Hand-held device
2 Housing
3 Cartridge
4 Cartridge head
5 Valve tube
6, 7 Annular part
8 Mouthpiece
9 Mouthpiece closure cap
10 Support section
11 Flow channel
12 Counter mechanism
13 Housing
14 Step-by-step indexing finger star
15 Hub
16 Viewing window
17 Air channel
18 Spray nozzle
19 First housing base
20 Annular space
21 Support part
22 Wall
23 Support part cover
24 Cartridge base
25 Mandrel
26 Spring
27 Section
28 Recess
29 Eccentric cam
30 Cap extension
31 Axial stump
32 Axial receptacle
33 Stop
34 Cantilever
35 Valve flap
36 Flap base
37 Second housing base
38 Flap chamber
39 Restoring arm
40 Support block
41 Stop part
42 Stop extension
43 Breakthrough
44 Inflow opening
45 Air passage
46 Air
47 Spray burst
48 Region
49 Spring
50 Docking part
51 Retaining pin
52 Recess
53 Release carriage
54 Guide block
55 Action section
56 Release section
57 Control surface
58 Spring arm 59 Release part
S Block
a Spacing
b Displacement distance
c Displacement distance
d Displacement distance
r Direction of movement
x Axis
y Axis of rotation
z Pivot axis

The invention claimed is:

1. A hand-held device for metered dispensing of sprayable substances, in particular inhaler medicaments, comprising:
   a housing having a mouthpiece,
   a cartridge configured to be displaced into a dispensing position by a pressure application relative to the housing,
   a spring supported on the housing and configured to act on the cartridge;
   wherein the cartridge is configured to be displaced initially into a ready-to-dispense position and when the cartridge is located in the ready-to-dispense position, a dispensing spray process can be triggered by sucking in,
   wherein the spring is configured such that displacement of the cartridge into the ready-to-dispense position can be executed by tensioning the spring, wherein the spring is configured to be displaced into a position for the cartridge to perform the spraying process, but is hindered from displacement by a counterforce, which counterforce can be deactivated by the user as a result of application of a negative pressure through the mouthpiece of the hand-held device,
   wherein a valve flap is configured to be moved by the negative pressure, and cancels a mechanical block (S) of the displacement of the cartridge from the ready-to-dispense position into a spray position, wherein the valve flap is arranged in a direction of movement (r) of the cartridge from a rest position into the spray position underneath a first air-permeable housing base of the housing,
   and wherein the first air-permeable housing base of the housing separates a chamber accommodating the valve flap from the mouthpiece in both the spray position and the ready-to-dispense position.

2. The hand-held device according to claim 1, wherein the valve flap is arranged in the direction of movement (r) of the cartridge from the rest position into the spray position underneath the cartridge.

3. The hand-held device according to claim 1, wherein the housing has a spray nozzle from which the substances exit in the spray position of the cartridge.

4. The hand-held device according to claim 3, wherein the spray nozzle is configured to deliver into an air channel formed partially by the mouthpiece.

5. The hand-held device according to claim 4, wherein the housing base is formed underneath the spray nozzle.

6. The hand-held device according to claim 5, wherein the housing base is formed as part of a lower wall of the air channel.

7. The hand-held device according to claim 1, wherein one or each of the air passages in the housing base is configured to be smaller than the valve flap.

8. The hand-held device according to claim 1, wherein the mechanical block (S) of the movement of the cartridge takes place by a stop.

9. The hand-held device according to claim 8, wherein the stop with the valve flap is pivotable to release the cartridge movement.

10. The hand-held device according to claim 8, wherein the cartridge acts upon a stop part.

11. The hand-held device according to claim 10, wherein the valve flap comprises the stop and wherein the stop part is configured to interact with the valve flap.

12. The hand-held device according to claim 10, wherein the stop part has a stop extension which passes through an air channel of the hand-held device.

13. The hand-held device according to claim 10, wherein the stop part is part of a counter mechanism which is configured to be moved by the cartridge during movement into the spray position.

14. The hand-held device according to claim 1, wherein the housing has a support part for the spring which is configured to be acted upon relative to the cartridge to tension the spring.

15. The hand-held device according to claim 14, wherein the hand-held device has a mouthpiece closure cap and wherein the mouthpiece closure cap is movement-coupled to the support part.

16. The hand-held device according to claim 15, wherein the movement coupling takes place by an eccentric application of a cap extension.

17. The hand-held device according to claim 15, wherein during a movement of the mouthpiece closure cap into an open position, the movement coupling results in a tensioning of the spring.

* * * * *